United States Patent [19]
Usher et al.

[11] Patent Number: 5,808,035
[45] Date of Patent: Sep. 15, 1998

[54] PROTECTED NUCLEOSIDE AND METHOD FOR ITS SYNTHESIS

[76] Inventors: David A. Usher, 144 Besemer Hill Rd., Ithaca, N.Y. 14850; Himanshu Rastogi, 8 Royal Crest Dr., Massachusetts, N.Y. 01752

[21] Appl. No.: 760,591

[22] Filed: Dec. 4, 1996

Related U.S. Application Data

[60] Provisional application No. 60/008,397 Dec. 8, 1995.
[51] Int. Cl.$^6$ .......................... C07H 21/02; C07H 19/10; C07H 19/20
[52] U.S. Cl. .................... 536/23.1; 536/25.1; 536/25.31; 536/25.34; 536/26.7; 536/26.71; 536/26.72; 536/26.74; 536/26.8; 536/27.6; 536/27.8; 536/27.81; 536/28.5; 536/28.53
[58] Field of Search ................................... 536/23.1, 25.1, 536/25.31, 25.34, 26.7, 26.71, 26.72, 26.74, 26.8, 27.6, 27.8, 27.81, 28.5, 28.53

[56] References Cited

U.S. PATENT DOCUMENTS

| | | | |
|---|---|---|---|
| 4,062,815 | 12/1977 | Hughes et al. | 530/307 |
| 4,415,732 | 11/1983 | Caruthers et al. | 536/26.7 |
| 4,469,863 | 9/1984 | Ts'o et al. | 536/23.1 |
| 4,725,677 | 2/1988 | Köster et al. | 536/26.7 |
| 5,026,838 | 6/1991 | Nojiri et al. | 536/26.7 |
| 5,214,135 | 5/1993 | Srivastava et al. | 536/26.7 |
| 5,256,549 | 10/1993 | Urdea et al. | 435/91 |
| 5,281,701 | 1/1994 | Vinayak | 536/25.34 |

FOREIGN PATENT DOCUMENTS

| | | | |
|---|---|---|---|
| WO 87/05906 A2 | 10/1987 | WIPO . | |
| 9317717 | 9/1993 | WIPO . | |
| 9505391 | 2/1995 | WIPO . | |
| 9520597 | 8/1995 | WIPO . | |

OTHER PUBLICATIONS

Rastogi et al., "A New 2'–Hydroxyl Protecting Group for the Automated Synthesis of Oligoribonucleotides," *Nucleic Acids Research*, 23(23), 4872–4877 (Dec. 11, 1995).

Pieles et al., "New and Convenient Protection System for Pseudouridine, Highly Suitable for Solid–Phase Oligoribonucleoitde Synthesis," *J. Chem. Soc. Perkin Transactions I*. (23), 3423–3429 (Dec. 7, 1994).

Sekine et al., "Oligoribuncleotide Synthesis By Use of the [[2–(Methylthio)phenyl]thio] methyl (MPTM) Group as the 2'–Hydroxyl Protecting Group," *Chemistry Letters*, (1), 121–124 (Jan. 1991).

Douglas et al., "An Approach Towards Thiol Mediated Labelling in the Minor Groove of Oligonucleotides," *Bioorganic & Medicinal Chemistry Letters*, 4(8), 995–1001 (Apr. 21, 1994).

Yamakage et al., "1–(2–Chloroethoxy)ethyl Group of the Protection of the 2'–Hydroxyl Group in the Synthesis of Oligoribonucleotides," *Tetrahedron Letters*, 30(46), 6361–6364 (1989).

Hagen et al., "General Synthesis of 2'(3')–O–Aminoacyl Oligoribonucleotides. The Protection of the Guanine Moiety," *J. Organic Chemistry*, 54(13), 3189–3195 (Jun. 23, 1989).

Takaru et al., "Synthesis of Oligoribonucleotides by Using 2'–O–(Methyl–2–methoxy) ethyl Nucleosides," *Chemistry letters*, (9), 1787–1790 (Sep. 1987).

Ito et al., "(Methoxyethoxy)methyl Group: New Amide and Hydroxyl Protecting Groups of Uridine in Oligonucleotide Synthesis," *J. Organic Chemistry*, 51(6), 931–933 (Mar. 21, 1986).

Takaku et al., "Synthesis of Ribooligonucleotides Using the 4–Methoxybenzyl Group as a New Protecting Group for the 2'–Hydroxyl Group," *J. Organic Chemistry*, 49(1), 51–56 (Jan. 13, 1984).

Beigelman et al., "Alternate Approaches to the Synthesis of 2'–O–Me Nucleosides," *Nucleosides and Nucleotides*, 14(3–5):421–25 (1995).

Sandström et al., "The Protection of the 2'hydroxyl Function in Oligoribonucleotide Synthesis," *Nucleosides and Nucleotides*, 4(1–2):177–81 (1985).

*Primary Examiner*—Douglas W. Robinson
*Assistant Examiner*—L. Eric Crane

[57] ABSTRACT

The present invention relates to a nucleoside having the formula:

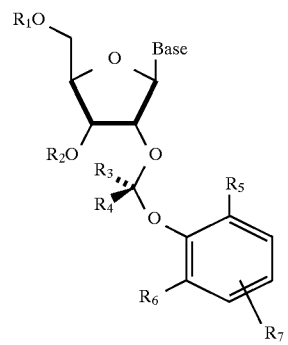

where
  $R_1$ is a hydrogen or a protecting group;
  $R_2$ is a hydrogen or a coupling group;
  $R_3$ and $R_4$ are each either a hydrogen or an alkyl group, where $R_3$ and $R_4$ can be connected in a ring;
  $R_5$ is a hydrogen, an alkyl group, or a carboxylic ester group;
  $R_6$ is a hydrogen, an alkyl group, or a carboxylic ester group;
  $R_7$ is a hydrogen, a nitro group, a halogen, a cyano group, or an alkyl group, where $R_7$ is attached at either position 4, 5 or 6; and
  Base is a protected heterocyclic base. Further, the present invention relates to a method of making the nucleoside and a method of oligomer synthesis utilizing the nucleoside.

35 Claims, No Drawings

PROTECTED NUCLEOSIDE AND METHOD FOR ITS SYNTHESIS

This application claims the benefit of U.S. Provisional patent application Ser. No. 60/008,397, filed Dec. 8, 1995.

FIELD OF THE INVENTION

The present invention relates to a protected nucleoside and a method for its synthesis.

BACKGROUND OF THE INVENTION

Discoveries made during the last fifteen years have revolutionized understanding of the diverse roles that RNA plays in biological systems. RNA has been shown to mediate precise cleavage and ligation reactions (Guerrier-Takada, et al., *Science*, 246:1578–1584 (1989); Cech, *Science*, 236: 1532–1539 (1987)), and, in addition to acting as an information carrier (mRNA and tRNA), RNA may take a more active catalytic role during protein synthesis (Noller, et al., *Science*, 256 (5062): 1416–19 (1992)). New ribozymes and receptors have been made through the selection or directed evolution of RNA. (Tuerk, *Science*, 249 (4968): 505–10 (1990); Robertson, et al., *Nature*, 344: 467–468 (1990); Famulok, et al., *Agnew. Chem. Int. Ed. Engl.*, 31: 979–988 (1992); Bock, et al., *Nature*, 355: 564–566 (1992); Bartel, et al., *Science*, 261 (5127): 1411–18 (1993); Sassanfar, et al., *Nature*, 364 (6437): 550–3 (1993); Doudna, et al., *Biochemistry*, 32 (8): 2111–15 (1993); Prudent, et al., *Science*, 264 (5167): 1924–1927 (1994); Morris, et al., *Proc. Natl. Acad. Sci., U.S.A.*, 91(26): 13028–13032 (1994); Dai, et al., *Science*, 267 (5195): 237–240 (1995)). Prior to the development of the translation apparatus and the consequent evolution of enzymes, the reactions of primitive cells may have been catalyzed primarily by RNA. (Crick, *J. Mol. Biol.*, 38:367–379 (1968); Orgel, *J. Mol. Biol.*, 38:381–393 (1968); Gilbert, *Nature*, 319:618 (1986)). Research in these and other areas would be helped by the development of simple and reliable methods for the rapid synthesis of oligoribonucleotides (Cohen, (ed.) *Oligonucleotides. Antisense Inhibition of Gene Expression*, Macmillan, London (1980)). However, methodologies for the chemical synthesis of oligoribonucleotides on solid phase supports have not kept pace with advances in DNA synthesis. Indeed, because of the difficulty of synthesizing RNA chemically, many workers use a machine to make DNA, and then transcribe the DNA using T7 RNA polymerase. (Milligan, et al., *Nucleic Acids Res.*, 15: 8783–8798 (1987)). This method has its own problems and limitations. (Scaringe, S.A., et al., *Nucleic Acids Res.*, 18(18): 5433–5441 (1990) ("Scaringe")).

For successful chemical synthesis of oligoribonucleotides, the hydroxyl group at the 2' position of ribonucleosides has to be suitably protected. A good 2'-OH protecting group must satisfy several requirements. Firstly, it must be stable to the acidic conditions employed for repeated removal of dimethoxytrityl ("DMTr") groups (the most common 5'-OH protecting group used in automated DNA and RNA synthesis). Secondly, it should be stable to the alkaline conditions that are used to cleave the completed chain from the solid support and remove the base and phosphate protecting groups. Thirdly, it should be removable at the end of the synthesis under sufficiently mild conditions that there is no modification of the nucleoside bases or cleavage or isomerization of the internucleotide linkages. Fourthly, the 2'-OH protecting group should not be so bulky that long coupling times are required. Finally, the reagents employed for cleavage of the 2'-OH protecting group should not make purification and isolation of fully deprotected RNA too cumbersome or time-consuming.

The use of an acetal as a 2'-OH protecting group appears to have many advantages. Acetals are stable to alkaline conditions and can be hydrolyzed using dilute acids. This makes purification of synthetic oligoribonucleotides by reverse phase high performance liquid chromatography ("HPLC") fairly straightforward. About twenty-five years ago, Reese and co-workers developed the tetrahydropyranyl ("Thp") group (1) (Griffin, et al., *Tetrahedron*, 24(2): 639–662 (1968)) and the 4-methoxytetrahydropyran-4-yl ("Mthp") group (2) (Reese, *Tetrahedron*, 26(4): 1023–1030 (1970)).

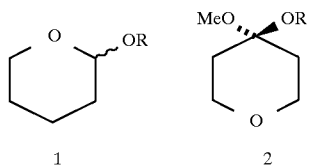

(For formulae 1 to 7, R is an nucleoside joined at its 2' position.) However, it was later found that neither of these groups is fully compatible with use of 5'-DMTr, as they are too acid labile. (Christodoulou, et al., *Tetrahedron Lett.*, 27 (13): 1521–1522 (1986)). In order to increase the acid stability of these protecting groups, Reese and co-workers designed two new acetals: 1-(2-chloro-4-methylphenyl)-4-methoxypiperidin-4-yl ("Ctmp") (3) (Reese, et al., *Tetrahedron Lett.*, 27 (20): 2291–2294 (1986)) and 1-(2-fluorophenyl)-4-methoxypiperidin-4-yl ("Fpmp") (4) (Reese, et al., *J. Chem. Soc., Perkin Trans.* 1, 2881–2885 (1988)).

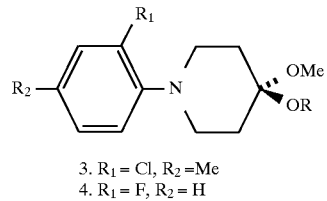

3. $R_1 = Cl, R_2 = Me$
4. $R_1 = F, R_2 = H$

With these two groups, protonation of the piperidine nitrogen slows the rate of acetal hydrolysis and makes it relatively pH-independent between 0.5 and 2.5. Fpmp is on average 1.3 times more stable than the Ctmp group in the pH range 0.5–1.5, and nucleoside phosphoramidites protected with Fpmp have been made commercially available.

Tetrahydrofuranyl ("Thf") (5) has been used in conjunction with DMTr for the synthesis of oligoribonucleotides containing up to eight bases (Tanaka, et al., *Chem. Pharm. Bull.*, 34(10): 4126–4132 (1986)).

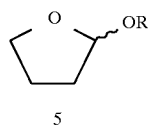

5

In this synthesis, DMTr groups were cleaved using 1M $ZnBr_2$ in dichloromethane:propan-2-ol in a ratio of 85:15.

Other acetals that have been developed as protecting groups for the 2'-OH of ribonucleosides are 1-(2-chloroethoxy)ethyl ("Cee") (6) (Yamakage, et al., *Tetrahedron Lett.*, 30(46): 6361–6364 (1989)), and 3-methoxy-1, 5-dicarbomethoxy-pentan-3-yl ("MDMP")(7) (Sandström, et al., *Acta Chem. Scand*, B 39: 273–290 (1985)).

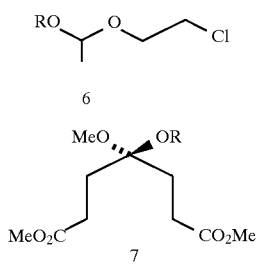

With the latter acetal, the ester groups are converted into the corresponding amides by treatment with concentrated ammonia. This speeds up the acetal hydrolysis by a factor of 17. However, even in the more stable ester form, a MDMP-protected nucleoside is slightly less stable to acid than a Mthp protected nucleoside. Id.

Recently there has been reported an acetaldehyde acetal that is relatively stable to acid, but which undergoes DBU-catalyzed elimination to a form that hydrolyzes in acid about 5 times faster than before the DBU treatment (Pfleiderer, et al., *Nucleic Acids Symp. Ser.*, 31: 143–144 (1994)).

At present, the most widely used protecting group for the 2'-OH of ribonucleosides is tert-butyldimethylsilyl ("TBDMS") (Scaringe; Hakimelahi, et al., *Can. J. Chem.*, 60: 1106 (1982); Wincott, et al., *Nucleic Acids Res*, 23(14): 2677–2684 (1995) ("Wincott")). This protecting group is usually cleaved with a 1M solution of tetrabutylammonium fluoride ($Bu_4NF$) in tetrahydrofuran. An excess of $Bu_4NF$ is commonly employed to ensure complete cleavage of the 2'-O-TBDMS groups, but this makes purification of the deprotected RNA difficult and time-consuming. A better reagent for the cleavage of TBDMS appears to be triethylamine hydrofluoride (TEA.3HF) (Gasparutto, et al., *Nucleic Acids Res.*, 20(19): 5159–5166 (1994) ("Gasparutto"); Westman, et al., *Nucleic Acids Res.*, 22(12):2430–2431 (1994)). As disclosed in Wincott, with N-methylpyrrolidone as a solvent, this reagent gives complete deprotection in 1.5 hours at 65° C. However, the TBDMS group is bulky, and, when N,N-diisopropyl phosphoramidites are used with tetrazole as the activating agent, a coupling time of around 10 minutes is required. (*Applied Biosystems User Bulletin*, 53: 1–7 (1989)). The use of 5-ethylthio-1H-tetrazole as the activator allows the coupling time to be reduced to 5 minutes (Wincott). Alternatively, the coupling time can be reduced to 2 minutes if N-ethyl-N-methyl phosphoramidite nucleosides are used (Gasparutto).

Since currently used protecting groups are difficult to remove during the deprotection step, the art has need for development of improved protecting groups The present invention is directed toward meeting this objective.

SUMMARY OF THE INVENTION

The present invention relates to a nucleoside having the formula:

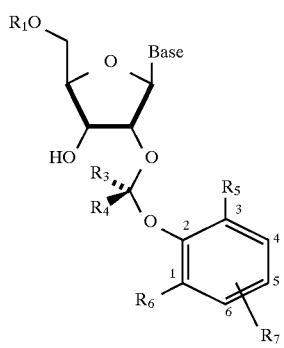

where
$R_1$ is a hydrogen or a protecting group;
$R_2$ is a hydrogen or a coupling group;
$R_3$ and $R_4$ are each either a hydrogen or an alkyl group, where $R_3$ and $R_4$ can be connected in a ring;
$R_5$ is a hydrogen group, an alkyl group, or a carboxylic ester group;
$R_6$ is a hydrogen, an alkyl group, or a carboxylic ester group;
$R_7$ is a hydrogen, a nitro group, a halogen, a cyano group, or an alkyl group, where $R_7$ is attached at either position 4, 5 or 6; and
Base is a protected heterocyclic base.

Another aspect of the present invention relates to a nucleoside having the formula:

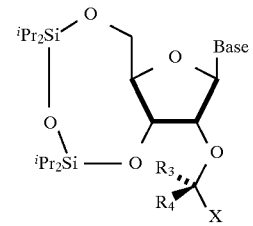

where $R_3$ and $R_4$ are each either a hydrogen or an alkyl group, where $R_3$ and $R_4$ can be connected in a ring;
X is either a thiomethyl group or an oxyethyl group; and
Base is a protected heterocyclic base.

Yet another aspect of the present invention relates to a nucleoside having the formula:

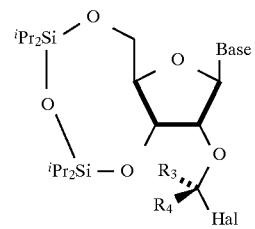

where $R_3$ and $R_4$ are each either a hydrogen or an alkyl group, where $R_3$ and $R_4$ can be connected in a ring;
Hal is any halogen; and
Base is a protected heterocyclic base.

Yet another aspect of the present invention relates to a method of producing a fully protected nucleoside comprising:
providing a 5'-OH protected nucleoside having the formula:

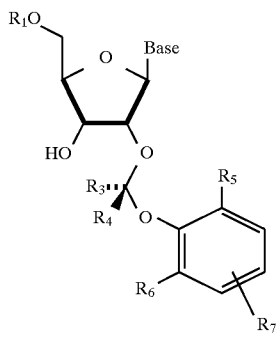

where
R$_1$ is a hydrogen or a protecting group;
R$_3$ and R$_4$ are each either a hydrogen or an alkyl group, where R$_3$ and R$_4$ can be connected in a ring;
R$_5$ is a hydrogen, an alkyl group, or a carboxylic ester group;
R$_6$ is a hydrogen, an alkyl group, or a carboxylic ester group;
R$_7$ is a hydrogen, a nitro group, a halogen a cyano group, or an alkyl group, where R$_7$ is attached at either position 4, 5 or 6; and
Base is a protected heterocyclic base;

providing a coupling group; and reacting the 5'-OH protected nucleoside and the coupling group under conditions effective to produce the fully protected nucleoside having the formula:

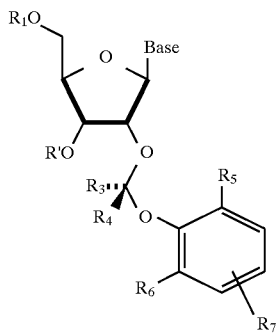

where
R$_1$ is a hydrogen or a protecting group;
R' is a coupling group;
R$_3$ and R$_4$ are each either a hydrogen or an alkyl group, where R$_3$ and R$_4$ can be connected in a ring;
R$_5$ is a hydrogen, an alkyl group, or a carboxylic ester group;
R$_6$ is a hydrogen, an alkyl group, or a carboxylic ester group;
R$_7$ is a hydrogen, a nitro group, a halogen a cyano group, or an alkyl group, where R$_7$ is attached at either position 4, 5 or 6; and
Base is a protected heterocyclic base.

DETAILED DESCRIPTION OF THE INVENTION

The present invention relates to a nucleoside having the formula:

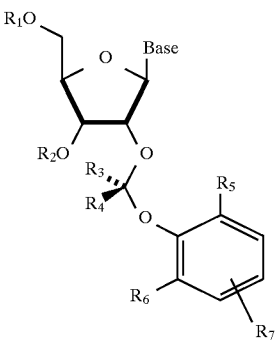

where
R$_1$ is a hydrogen or a protecting group;
R$_2$ is a hydrogen or a coupling group;
R$_3$ and R$_4$ are each either a hydrogen or an alkyl group, where R$_3$ and R$_4$ can be connected in a ring;
R$_5$ is a hydrogen, an alkyl group, or a carboxylic ester group;
R$_6$ is a hydrogen, an alkyl group, or a carboxylic ester group;
R$_7$ is a hydrogen, a nitro group, a halogen, a cyano group, or an alkyl group, where R$_7$ is attached at either position 4, 5 or 6; and
Base is a protected heterocyclic base.

There are conflicting requirements for an acetal-based 2'-hydroxyl protecting group. On the one hand, it should be stable towards the acid that is used repeatedly for removal of DMTr groups during chain synthesis. On the other hand, it must be sufficiently labile so that its removal at the end of the synthesis can be accomplished in mild acid without isomerization or cleavage of the internucleotide bonds. Further, a 2' hydroxyl protecting group must stay in place during the ammonia deprotection step that is typically used at the end of oligomer synthesis. A free 2'-hydroxyl can deprotonate in a base, and the resulting alkoxide anion can attack the neighboring phosphate diester, causing chain cleavage.

The best way of meeting these requirements in the nucleoside of the present invention is to use a convertible protecting group, i.e. one that is stable to acid during chain synthesis, but which is changed by the standard ammonia deprotection step to a form that falls off readily in mild acid. In the bis ester form, this 2'-OH protecting group is stable to the conditions employed during solid phase synthesis of RNA. In addition, the protecting group is easily removed at the end of the RNA synthesis. This deprotection is achieved in two steps. First, the esters are hydrolyzed in a base, then the pH of the solution is adjusted to between 2 and 3. Conversion of the bis ester to the bis carboxylic acid markedly increases the acid lability of the acetal. Dunn, et al *J. Am. Chem. Soc.*, 92(8):2410–2416 (1970), which is hereby incorporated by reference. This increased rate of hydrolysis has been variously ascribed to intramolecular general acid catalysis (Kirby, et al, *J. Chem. Soc., Chem. Commun.* (6):707–708 (1994), which is hereby incorporated by reference), or to electrostatic facilitation of protonation of the acetal oxygen (Dunn, et al, *J. Am. Chem. Soc.*, 93 (22):5725–5731 (1971), which is hereby incorporated by reference).

The reactivity of the acetal can be further modified by additional substitutents on the acetal or benzene ring, and its design should allow for short coupling times as it appears less hindered than other acetals or TBDMS.

The method of producing the fully protected nucleoside of the present invention includes providing a 5'-OH protected nucleoside having the formula:

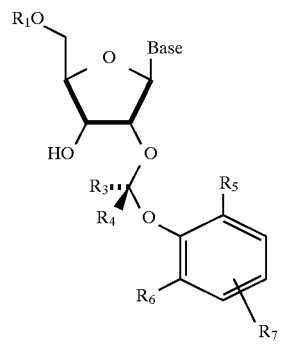

where
- $R_1$ is a hydrogen or a protecting group;
- $R_3$ and $R_4$ are each either a hydrogen or an alkyl group, where $R_3$ and $R_4$ can be connected in a ring;
- $R_5$ is a hydrogen, an alkyl group, or a carboxylic ester group;
- $R_6$ is a hydrogen, an alkyl group, or a carboxylic ester group;
- $R_7$ is a hydrogen, a nitro group, a halogen a cyano group, or an alkyl group, where $R_7$ is attached at either position 4, 5 or 6; and
- Base is a protected heterocyclic base. A coupling group, such as, but not limited to, 2-cyanoethyl-N,N-diisopropyl phosphoramidite, is provided and reacted with the 5'-OH protected nucleoside at from 15° to 30° C. for 1 to 3 hours at about atmospheric pressure under conditions effective to produce the fully protected nucleoside having the formula:

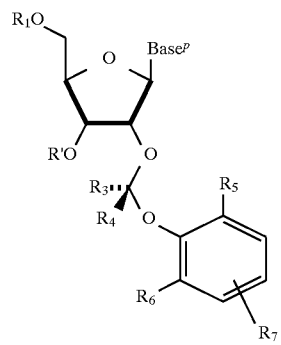

where R' is a coupling group and $R_1$, $R_3$, $R_4$, $R_5$, $R_6$, $R_7$, and Base are as defined above.

Providing the $5^1$-OH protected nucleoside includes providing a 2'-OH protected nucleoside having the formula:

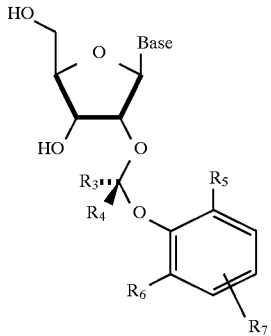

where $R_3$, $R_4$, $R_5$, $R_6$, $R_7$, and Base are as defined above. A protecting group is provided and reacted with the 2'-OH protected nucleoside at from 15° to 30° C. for 1 to 3 hours at about atmospheric pressure under conditions effective to produce the 5'-OH protected nucleoside.

Providing the 2'-OH protected nucleoside includes providing a nucleoside having the formula:

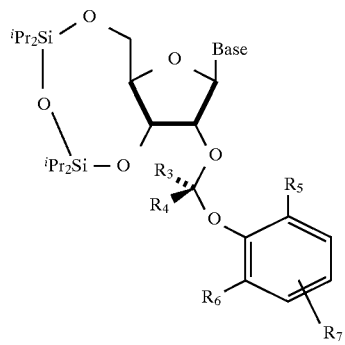

where $R_3$, $R_4$, $R_5$, $R_6$, $R_7$, and Base are as defined above. Tetrabutyl ammonium fluoride is provided and reacted with the nucleoside under condition effective to produce the 2'-OH protected nucleoside.

Providing the nucleoside includes providing a haloalkyl ether having the formula:

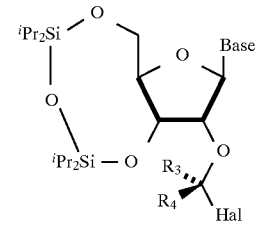

where $R_3$ and $R_4$ and base are as defined above and Hal is any halogen. A salt of a hydroxy compound, preferably a phenol, is provided and reacted with the haloalkyl ether at from 15° to 30° C. for 30 to 60 minutes at about atmospheric pressure under conditions effective to produce the nucleoside.

Providing the haloalkyl ether includes providing an ether having the formula:

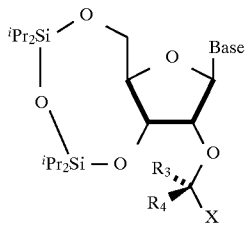

where $R_3$, $R_4$, and Base are as defined above and X is either thiomethyl or oxyethyl. A halogenating group is provided and reacted with the ether at from 15° to 30° C. for 30 to 90 minutes at about atmospheric pressure under conditions effective to produce the haloalkyl ether.

Providing the haloalkyl ether further includes providing a base protecting group. The base is protected with any protecting group useful to mask any acidic hydrogens. Preferred protecting groups are benzoyl groups, phenoxyacetyl groups, methoxyethoxymethyl groups, dimethylformamidine groups, and isobutyrl groups. The ether is reacted with the base protecting group at from 15° to 30° C. for 8 to 16 hours at about atmospheric pressure under conditions effective to produce the haloalkyl ether.

Providing the ether includes providing a monomer having the formula:

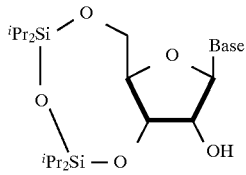

where base is a heterocyclic base. Either ethyl vinyl ether, or DMSO with acetic acid and acetic anhydride, is provided and reacted with the monomer at from 15° to 30° C. for 5 to 9 hours at about atmospheric pressure under conditions effective to produce the ether.

Providing a monomer includes providing a compound having the formula:

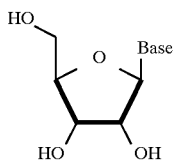

where base is a heterocyclic base and providing 1,3-dichloro-1,1,3,3, tetraisopropyldisiloxane and reacting the compound and the 1,3-dichloro-1,1,3,3, tetraisopropyldisiloxane under conditions effective to produce the monomer.

Further, the nucleoside can be utilized to produce an oligomer, where the method of oligomer synthesis includes providing a nucleoside on a solid support and repeatedly reacting it with a nucleoside having the formula:

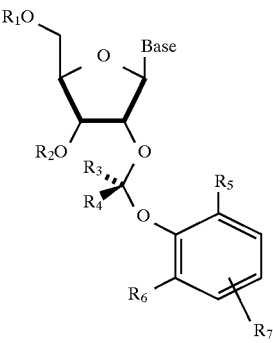

where
$R_1$ is a hydrogen or a protecting group;
$R_2$ is a hydrogen or a coupling group;
$R_3$ and $R_4$ are each either a hydrogen or an alkyl group, where $R_3$ and $R_4$ can be connected in a ring;
$R_5$ is a hydrogen, an alkyl group, or a carboxylic ester group;
$R_6$ is a hydrogen, an alkyl group, or a carboxylic ester group;
$R_7$ is a hydrogen, a nitro group, a halogen, a cyano group, or an alkyl group, where $R_7$ is attached at either position 4, 5 or 6; and
Base is a protected heterocyclic base, at 15° to 30° C. for 1 to 10 minutes at about atmospheric pressure under conditions effective to produce the oligomer having the structure:

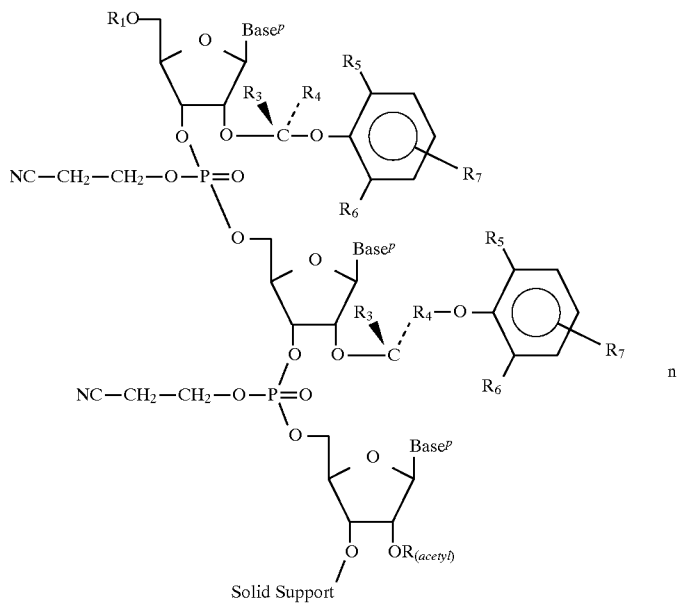
n = 0 to 100
A preferred embodiment for the synthesis of fully protected nucleoside is depicted below.
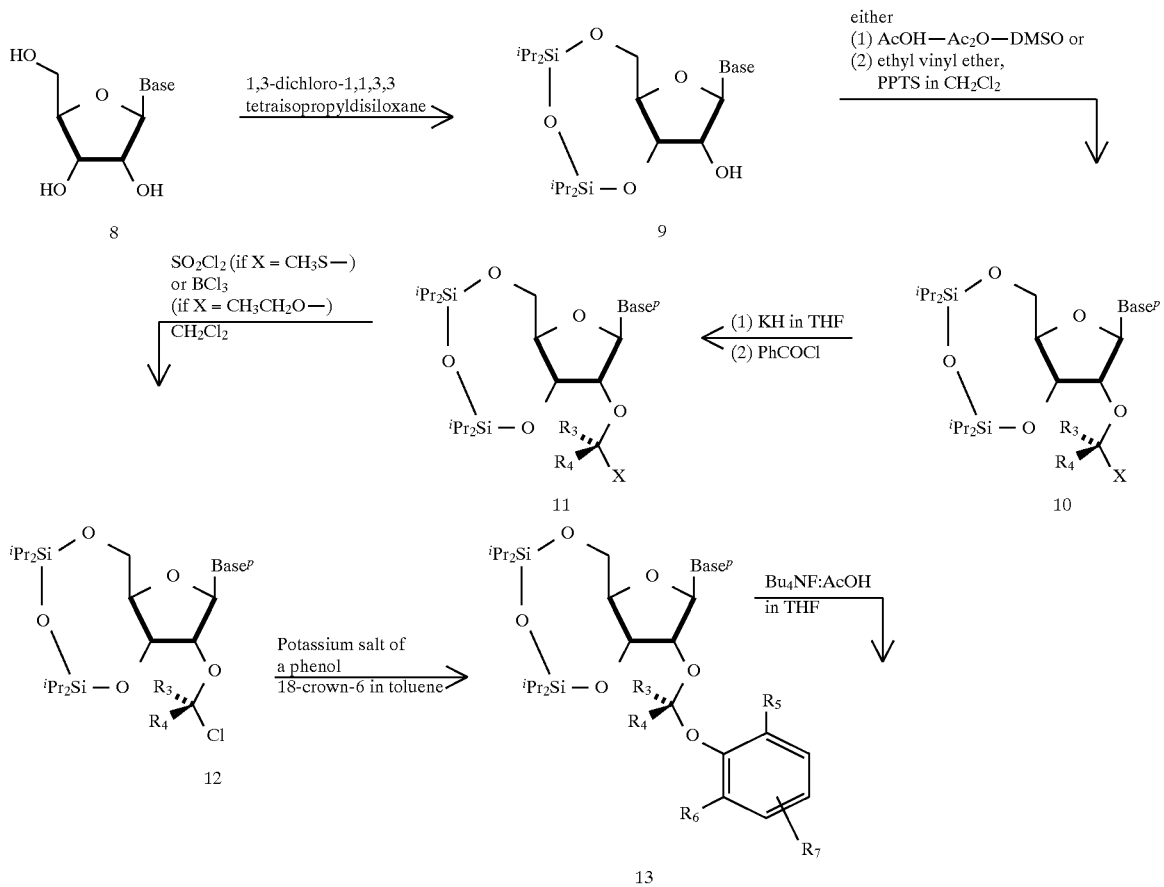

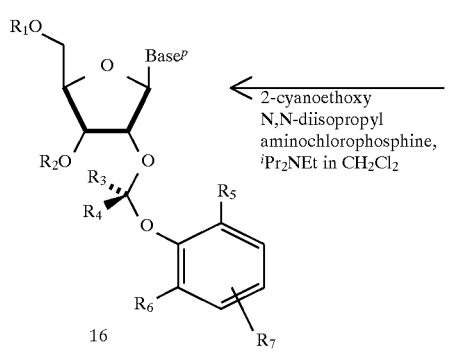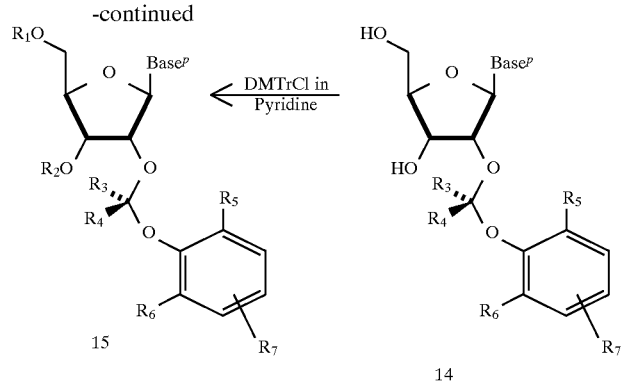

Pursuant to this synthesis, a nucleoside (8) is reacted with 1,3-dichloro-1,1,3,3-tetraisopropyldisiloxane under conditions effective to provide the monomer (9).

The monomer (9), such as, but not limited to, 3',5'-O-(tetraisopropyldisiloxan-1,3-diyl)uridine (9) is converted to its 2'-O-methylthiomethyl ether (10) by reaction with dimethylsulfoxide ("DMSO"), acetic anhydride and acetic acid, under conditions effective to produce the 2'-O-methylthiomethyl ether. Pojer, et al *Tetrahedron Lett.* 35:3067–3068 (1976); Zavgorodny, et al, *Tetrahedron Lett.*, 32(51):7593–7596 (1991), which are hereby incorporated by reference. Alternatively, acetaldehyde acetals are produced by forming a ethoxyethyl ether instead of a methylthiomethyl ether.

To produce the ethoxyethyl compound, monomer (9) is reacted with ethyl vinyl ether under conditions effective to produce the ethoxyethyl ether (10).

The 2'-O-methylthiomethyl or ethoxyethyl ether (10) is reacted with a benzoyl protecting group, such as benzoyl chloride, under conditions effective to produce the protected base (11). (Inoue, et al, *Nucleic Acids Res.*, 15(15):6131–6148 (1987)), which are hereby incorporated by reference.

The methylthiomethyl or ethoxyethyl ether (10) is cleaved with sulfuryl chloride or $BCl_3$ respectively, to yield a chloromethyl ether or chloroethyl ether, respectively (12). Antonsen, et al, *Acta Chemica Scan.*, 43:56–61 (1989), which is hereby incorporated by reference. The identity of the chloroalkyl ether is confirmed by treating it with $Bu_4NOAc$ and isolating the acetoxymethyl ether formed. Rastogi, Ph.D. Thesis, Cornell University, Ithaca, N.Y. (1995), which is hereby incorporated by reference. This is achieved by reacting the chloroalkyl ether (12) with tetrabutylammonium acetate in methylene chloride at 15° to 20° C. for 15 to 60 minutes at about atmospheric pressure under conditions to remove the Cl group.

A potassium salt of a phenol is needed for the next step in the reaction. The preferred potassium salt of a phenolic ester is made in two steps starting from commercially available 2-methoxyisophthalic acid. It is first reacted with trimethyloxonium tetrafluoroborate ($Me_3OBF_4$) and diisopropylethylamine ("$^iPr_2NEt$") under conditions effective to produce dimethyl 2-methoxyisophthalate. Gerecke, et al. *Helv. Chim. Acta.*, 59:2551 (1976), which is hereby incorporated by reference. Then, the methyl ether is cleaved with $BCl_3$ under conditions effective to yield dimethyl 2-hydroxyisophthalate. The potassium salt of dimethyl 2-hydroxyisophthalate is prepared by treating it with potassium hydride (KH) in toluene for about 20 minutes at about 0° C. under conditions effective to produce the potassium salt.

The chloroalkyl ether (12) is reacted with this potassium salt in the presence of 18-crown-6 under conditions effective to produce the nucleoside (13). If the base $N^3$ was not protected by the step discussed above, this reaction fails.

Potassium salts of a phenol or other hydroxylic nucleophile may be added to the haloalkyl ether (12) to produce the nucleoside (13). Preferred potassium salts include the potassium salt of dimethyl- or di-(2-cyanoethyl)-2-hydroxyisophthalate, the potassium salt of an appropriately substituted salicylate ester, the potassium salt of methyl or 2-cyanoethyl salicylate.

When the chloromethyl ether (12) is treated with the sodium salt of methyl salicylate in DMF, a more polar product formed which was not characterized. This suggests that the chloromethyl ether was decomposing under the alkaline reaction conditions. A similar problem had been encountered in the methoxymethylation of some chalcones with NaH and $ClCH_2OMe$ in DMF. Rall, et al, *Tetrahedron Lett.*(13):1033–1036 (1976), which is hereby incorporated by reference. However, when the potassium salt of a chalcone was treated with $ClCH_2OMe$ in dry $CH_3CN$ in the presence of 18-crown-6, the desired methoxymethyl ether was formed in good yield.

The nucleoside (13) is treated with tetrabutyl ammonium fluoride under conditions effective to cleave the disiloxane group and produce the 2'-OH protected nucleoside (14).

It is especially desirable to produce the following compounds by the synthesis described above. When the chloromethyl ether (12) is reacted with the potassium salt of dimethyl 2-hydroxyisophthalate ester, a compound is produced having the formula (14):

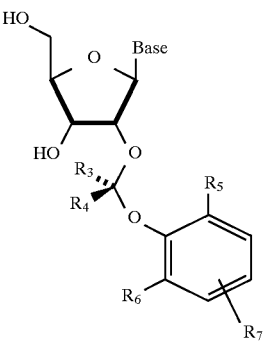

where $R_3$, $R_4$, and $R_7$ are hydrogen and $R_5$ and $R_6$ are $CO_2CH_3$.

When the chloroethyl ether (12) is reacted with a potassium salt of methyl salicylate, a compound is produced having the above formula (14) where one of either $R_3$ or $R_4$ is an alkyl and the other is hydrogen, $R_5$ is $CO_2CH_3$, and $R_6$ and $R_7$ are hydrogen.

When the chloromethyl ether (12) is reacted with the potassium salt of an appropriately substituted salicylate ester, a compound is produced having the formula (14) where $R_3$ or $R_4$ are hydrogen, $R_5$ is $CO_2CH_3$ or $CO_2CH_2CH_2CN$, and $R_6$ is hydrogen or $C(CH_3)_3$, and $R_7$ is hydrogen.

The 2'-OH protected nucleoside (14) is reacted with a protecting group, such as, but not limited to a DMTr group, to produce a 5-OH protected nucleoside (15). The 5-OH protected nucleoside (15) is next converted to the fully protected nucleoside (16) by reacting the 5'-OH protected nucleoside (15) with a coupling group, such as but not limited to, 2-cyanoethoxy N,N,-diisopropylaminochlorophosphine under conditions effective to produce the fully protected nucleoside (16).

Acetaldehyde acetals form a more stable carbocation in the rate determining step for hydrolysis, and are more acid labile than formaldehyde acetals. For example, the diethyl acetal of acetaldehyde hydrolyzes 6,000 times faster than the corresponding formaldehyde acetal. Cordes, *Progress in Physical Organic Chemistry*, 4, 1–44 (1967), which is hereby incorporated by reference. However, an acetaldehyde acetal introduces a new stereogenic center, and this gives two diastereomers of a protected nucleoside. The $^1$H NMR spectrum shows that the two diastereomers are found in the present invention in the ratio of 2:3. Hydrolysis studies indicated that the two diastereomers have very different hydrolytic behavior. Initial indications are that one of the diastereomers could be an effective 2'-hydroxyl protecting group.

Although synthesis of the fully protected nucleoside (16) from monomer (9) presently takes seven steps, the group is achiral, relatively unhindered, and an advantageous additional to the list of 2'-OH protecting groups. It is highly desirable to shorten deprotection times further, while still maintaining adequate stability during chain synthesis. This may be achieved by introducing an electron-withdrawing substituent on the benzene ring. Craze, et al, *J. Chem. Soc., Perkin Trans.* 2:61–66 (1974), which is hereby incorporated by reference.

The fully protected nucleoside is useful in the synthesis of RNA and other oligomers. In the synthesis, a machine synthesizer is preferably utilized where a standard nucleoside is provided on a solid support at the 3'-terminus via either its 2' or 3' hydroxyl with a succinate linker, while the other hydroxyl is protected with an acetyl group. The 5' hydroxyl is protected with a dimethyoxytrityl ("DMTr"). Further, the base is protected by any suitable protecting group. The DMTr group is removed from the 5' hydroxy and the standard nucleoside on the solid support is contacted with a fully protected nucleoside having the formula:

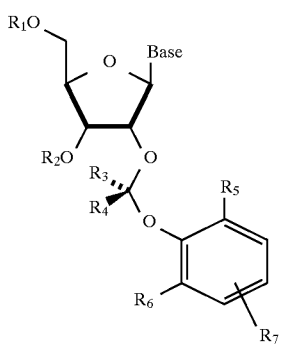

where
$R_1$ is a protecting group;
$R_2$ is a coupling group;
$R_3$ and $R_4$ are each either a hydrogen or an alkyl group, where $R_3$ and $R_4$ can be connected in a ring;
$R_5$ is a carboxylic ester group;
$R_6$ is a hydrogen, an alkyl group, or a carboxylic ester group;
$R_7$ is a hydrogen, a nitro group, a halogen group, a cyano group, or an alkyl group, where $R_7$ is attached at either position 4, 5 or 6; and
Base is a protected heterocyclic base.

The nucleosides are kept in contact for 1 to 10 minutes at 15° to 30° C. at atmospheric pressure under conditions effective to couple the two nucleosides. It is especially desirable that the nucleosides be kept in contact for less than five minutes. By repeatedly reacting the nucleoside on the solid support with additional fully protected nucleosides, the oligomer is formed.

The present invention is further described by reference to the following non-limited examples.

EXAMPLES

Materials and Methods

Uridine and 1,3-dichloro-1,1,3,3-tetraisopropyldisiloxane were supplied by Sigma (St. Louis, Mo.). All other chemicals were obtained from Aldrich Chemical Company (Milwaukee, Wis.) and were used without further purification. The solvents anhydrous acetonitrile and tetrahydrofuran were purchased from Aldrich Chemical Company. Dichloromethane, toluene, and pyridine were refluxed over calcium hydride for 4 hours, distilled and stored over freshly activated 4 Å molecular sieves. Thin layer chromatography was performed on EM precoated silica gel 60 $F_{254}$ aluminum plates. Column chromatography (Still, et al., *J. Org. Chem.*, 43(14):2923–2925 (1978), which is hereby incorporated by reference) was done on silica gel 32–63 supplied by ICN Biomedicals, Irvine, Calif. High performance liquid chromatography ("HPLC") was performed on Waters Nova-Pak 4μm C-18 spherical silica in a Radial-Pak 5×100 mm cartridge, using a Waters RCM compression module. A Hewlett Packard 3396 Series II integrator was used to calculate and record the peak areas. $^1$H NMR spectra were recorded on a Varian XL-200 spectrometer. Chemical shift values δ are reported relative to tetramethylsilane. $^{31}$P NMR spectra were recorded on a Varian VXR-400 spectrometer 85% phosphoric acid was used as an external standard. Oligonucleotide synthesis was carried out on an ABI Model #391 Synthesizer.

Example 1

3',5'-O-(Tetraisopropyldisiloxane-1, 3-diyl)uridine (9)

3',5'-O-(Tetraisopropyldisiloxane-1,3-diyl) uridine (9) was prepared according to Markiewicz, *J Chem. Res. (M)*, 181–197 (1979), which is hereby incorporated by reference. Uridine (600 mg, 2.64 mmol) was dissolved in dry pyridine (10 ml), and 1,3-dichloro-1,1,3,3-tetraisopropyldisiloxane (0.9 ml, 2.82 mmol, 1.15 equiv.) was added. The solution was stirred at room temperature for 3 hours, diluted with EtOAc (20 ml) and extracted once with 5% NaHCO$_3$ (20 ml). The aqueous layer was back-extracted with ethyl acetate ("EtOAc") (2×15 ml). Organic extracts were combined, washed once with brine (15 ml) and dried over anhydrous MgSO$_4$. The solvent was evaporated to give a light yellow oil. Purification of the crude product by column chromatography on silica gel with 1:1 EtOAc:petroleum ether gave the title compound as a white foam. Yield: 1.2 g (93%). $^1$H NMR (CDCl$_3$)δ:8:8 (br.s, 1 H, NH), 7.71 (d, 1 H, H5 or H6, $J_{5,6}$=8 Hz), 5.73(s, 1 H, H1'), 5.70 (d, 1 H, H5 or H6, $J_{5,6}$=8 Hz), 4.38–3.96 (m, 5 H, H2', H3', H4' and H5'), 3.12 (br.s, 1 H, 3'-OH), 1.2–0.9 (m, 28 H, isopropyls).

Example 2

2'-O-Methylthiomethyl-3',5'-O-(tetraisopropyldisiloxane-1,3-diyl)uridine (10)

3',5'-0-(Tetraisopropyldisiloxane-1,3-diyl)uridine, prepared according to Example 1 (1.13 g, 2.3 mmol) was dissolved in DMSO (7.2 ml). Acetic acid (7.3 ml) and acetic anhydride (4.7 ml) were added, and the solution was stirred overnight at room temperature. It was then cooled in an ice bath, and Et$_3$N (10 ml) added to quench the reaction. It was diluted with EtOAc (25 ml) and extracted once with 5% NaHCO$_3$ (20 ml). The aqueous layer was back-extracted with EtOAc (2×15 ml). The organic layers were pooled, washed once with brine (10 ml), and then dried over anhydrous MgSO$_4$.

The crude product was purified by column chromatography using 1:2 EtOAc:petroleum ether as the eluting solvent. It was obtained as a white foam. Yield: 0.91 g (81%). $^1$H NMR (CDCl$_3$) δ: 8.5 (br.s, 1 H, NH), 7.91 (d, 1 H, H5 or H6, $J_{5,6}$=8 Hz), 5.72 (s, 1 H, H1'), 5.68 (d, 1 H, H5 or H6, $J_{5,6}$=8 Hz), 4.98 (s, 2 H, OCH$_2$S), 4.38–3.94 (m, 5 H, H2', H3', H4' and H5'), 2.18 (s, 3 H, SCH$_3$), 1.2–0.9 (m, 28 H, isopropyls).

Example 3

N$^3$-Benzoyl-2'-O-methylthiomethyl-3',5'-O-(tetraisopropyldisiloxane-1,3-diyl)uridine (11)

KH (35 wt % oil dispersion, 303 mg, 2.6 mmol, 1.4 equiv.) was suspended in dry THF (8 ml) and the suspension cooled in an ice bath. The flask was flushed with argon, a solution of (10), prepared according to Example 2, (1.02 g, 1.86 mmol) in dry tetrahydrafuran ("THF") (2.5 ml) was added, and the suspension stirred at 0° C. for 15 minutes. Benzoyl chloride (0.35 ml, 3 mmol, 1.6 equiv.) was added, and the solution stirred overnight at room temperature. The crude product was purified by column chromatography. The column was eluted first with 85:15 petroleum ether:EtOAc (150 ml) and then with 7:3 petroleum ether:EtOAc. The pure product was obtained as a white foam. Yield: 0.97 g (80%). $^1$H NMR (CDCl$_3$) δ: 8.02 (d, 1 H, H5 or H6, $J_{5,6}$=8 Hz), 7.96–7.45 (5 H, aryl), 5.80 (d, 1 H, H5 or H6, $J_{5,6}$=8 Hz), 5.75 (s, 1 H, 1'), 4.90 (s, 2 H, OCH$_2$S), 4.40–3.95 (m, 5 H, H2', H3', H4' and H5'), 2.12 (s, 3 H, SCH$_3$), 1.2–0.9 (m, 28 H, isopropyls).

Example 4

Dimethyl 2-methoxyisophthalate

2-Methoxyisophthalic acid (320 mg, 1.63 mmol) was suspended in CH$_2$Cl$_2$ (6 ml) and N,N-diisopropylethylamine (0.68 ml, 3.9 mmol, 2.4 equiv.) was added. After 5 minutes, trimethyloxonium tetrafluoroborate (615 mg, 2.6 equiv.) was added, and the reaction mixture was stirred for 1 hour at room temperature. After evaporation of the solvent, column chromatography with 3:7 EtOAc:petroleum ether gave the product as a white solid. Yield: 330 mg (90%). $^1$H NMR (CDCl$_3$) δ: 7.93 (d, 2 H, aryl), 7.21 (t, 1 H, aryl), 3.94 (s, 9 H, OCH$_3$ and CO$_2$CH$_3$).

Example 5

Dimethyl 2-hydroxyisophthalate

Dimethyl 2-methoxyisophthalate, prepared according to Example 4, (279 mg, 1.24 mmol) was dissolved in dry CH$_2$Cl$_2$ (5 ml), and the flask was flushed with argon. Boron trichloride (1M solution in heptane, 1.2 ml) was added, and the solution was stirred under argon for 1 hour at room temperature. After evaporation of the solvent, chromatography with 3:7 EtOAc:petroleum ether gave the product as a white solid. Yield: 237 mg (91%). $^1$H NMR (CDCl$_3$) δ: 8.06 (d, 2 H, aryl), 6.94 (t, 1 H, aryl), 3.96 (s, 6 H, CO$_2$CH$_3$)

Example 6

N$^3$-Benzoyl-2'-O-(dimethyl 2-methoxyisophthalate)-3',5'-O-(tetraisopropyldisiloxane-1,3-diyl)uridine (13)

Compound (11), prepared according to Example 3, (190 mg, 0.29 mmol) was dissolved in dry CH$_2$Cl$_2$ (1.5 ml), and the flask was flushed with argon for 10 minutes. SO$_2$Cl$_2$ (1M solution in CH$_2$Cl$_2$, 0.35 ml, 1.2 equiv.) was added, and the solution was stirred at room temperature for 50 minutes under an argon atmosphere. Solvent was evaporated, and the chloromethyl ether (12) was obtained as an orange foam.

KH (35 wt % oil dispersion, 58 mg, 0.51 mmol, 1.72 equiv.) was suspended in dry toluene (10 ml) and the flask was flushed with argon. The suspension was cooled to 0° C., and a solution of dimethyl 2-hydroxyisophthalate (123 mg, 0.6 mmol, 2 equiv.) in dry toluene (0.5 ml) was added. The suspension was stirred for 15 minutes at 0° C., allowed to warm to room temperature, and 18-crown-6 (60 mg, 0.22 mmol, 0.75 equiv.) was added. A solution of chloromethyl ether (12) in dry CH$_2$Cl$_2$ (1 ml) was added slowly over a period of 5 minutes. The reaction mixture was stirred under argon for 45 minutes at room temperature, diluted with EtOAc (10 ml), and extracted once with water (10 ml). The aqueous layer was back-extracted with EtOAc (2×10 ml). Organic extracts were pooled, washed once with brine (5 ml), and dried over anhydrous MgSO$_4$. Solvent was evaporated and the crude product purified by column chromatography. The column was eluted first with 1:3 EtOAc:petroleum ether and then with 1:1 EtOAc:petroleum ether. The pure product was obtained as a white foam. Yield: 190 mg (81%). $^1$H NMR (CDCl$_3$) δ: 7.95–7.14 (8 H, aryl), 7.80 (d, 1 H, H5 or H6, $J_{5,6}$=8 Hz), 5.78 (d, 1 H, H5 or H6, $J_{5,6}$=8 Hz), 5.70 (s, 1 H, H1'), 5.41 (s, 2 H, OCH$_2$O), 4.42–3.90 (m, 5 H, H2', H3', H4' and H5'), 3.85 (s, 6 H, CO$_2$CH$_3$), 1.2–0.9 (m, 28 H, isopropyls).

Example 7

N$^3$-Benzoyl-2'-O-(dimethyl 2-methoxyisophthalate) uridine (14)

Compound (13), prepared according to Example 6, (175 mg, 0.21 mmol) was dissolved in THF (1.5 ml), and the flask was flushed with argon. Acetic acid (30 μl, 0.5 mmol, 2.5 equiv.) was added followed by Bu$_4$NF (1M solution in THF, 0.46 ml, 2.2 equiv.). The solution was stirred at room temperature for 10 minutes. The reaction mixture was diluted with EtOAc (10 ml) and extracted once with 5% NaHCO$_3$ (10 ml). The aqueous layer was back-extracted with EtOAc (3×10 ml). The organic extracts were combined, washed once with brine (10 ml), and then dried over anhydrous MgSO$_4$. The crude product was purified by column chromatography. The column was eluted first with 4:1 EtOAc:petroleum ether (150 ml) and then with 4% methanol in EtOAc. The product, which eluted with the second solvent system, was obtained as a white foam. Yield: 115 mg (96%). $^1$H NMR (CDCl$_3$) δ: 8.03–7.22 (8 H, aryl), 7.82 (d, 1 H, H5 or H6, J$_{5,6}$=8 Hz), 5.87 (s, 1 H, H1', J$_{1',2'}$=4.8 Hz), 5.83 (d, 1H, H5 or H6, J$_{5,6}$=8 Hz), 5.33 (AB quartet, 2 H, OCH$_2$O, J=4.4 Hz), 4.69 (t, 1 H, H2'), 4.47 (t, 1 H, H3'), 4.18 (m, 1 H, H4'), 3.92 (q, 2H, H5'), 3.89 (s, 6 H, CO$_2$CH$_3$).

Example 8

N$^3$-Benzoyl-2'-O-(dimethyl 2-methoxyisophthalate)-5'-O-(4,4'-dimethoxytrityl)uridine (15)

Compound (14), prepared according to Example 7, (137 mg, 0.24 mmol) was co-evaporated with dry pyridine (3×1 ml), dissolved in dry pyridine (1.5 ml), and mixed with 4,4'-dimethoxytrityl chloride (120 mg, 0.35 mmol, 1.5 equiv.). The reaction mixture was stirred for 2 hours at room temperature under argon, diluted with EtOAc (10 ml) and extracted once with 5% NaHCO$_3$ (10 ml). The aqueous layer was back-extracted with EtOAc (2×10 ml). The organic extracts were combined, washed once with brine (6 ml), and then dried over anhydrous MgSO$_4$. The crude product was purified by column chromatography. The column was eluted first with 2:3 EtOAc:petroleum ether and then with 7:3 EtOAc:petroleum ether. The pure product was obtained as a yellow foam. Yield: 190 mg (90%). $^1$H NMR (CDCl$_3$) δ: 8.09 (d, 1 H, H5 or H6, J$_{5,6}$=8 Hz), 8.01–7.20 (m, 17 H, aryl), 6.87 (d, 4 H, aryl), 6.04 (d, 1 H, H1'), 5.42 (AB quartet, 2H, OCH$_2$O, J=4.5 Hz), 5.36 (d, 1 H, H5 or H6, J$_{5,6}$=8 Hz), 4.67 (q, 1 H, H2' or 3'), 4.54 (m, 1 H, H2' or 3'), 4.19 (m, 1 H, H4'), 3.81 (s, 12 H, OCH$_3$ and CO$_2$CH$_3$) , 3.55 (m, 2 H, H5').

Example 9

N$^3$-Benzoyl-2'-O-(dimethyl 2-methoxyisophthalate)-3'-O-(2-cyanoethyl N,N-diisopropylphosphoramidite)-5'-O-(4,4'-dimethoxytrityl)uridine (16)

N$^3$-Benzoyl-2'-O-(dimethyl 2-methoxyisophthalate)-5'-O-(4,4'-dimethoxytrityl)uridine (15), prepared according to Example 8, (115 mg, 0.13 mmol) was co-evaporated with dry toluene (3×1 ml) and dried in vacuo for 4 hours. It was converted to the phosphoramidite by the method of Sinha et al., *Nucleic Acids Res.*, 12:4539–4557 (1984), which is hereby incorporated by reference. The crude product was purified by column chromatography. The column was first eluted with 35:65:2 EtOAc:petroleum ether:Et$_3$N (100 ml) to remove the excess phosphitylating reagent and then with 60:40:2 EtOAc:petroleum ether:Et$_3$N. The title compound was obtained as a white foam. Yield: 117 mg (84%). $^{31}$P NMR (CDCl$_3$) δ: 151.14 and 150.77.

Example 10

Dimer Synthesis

Two dimers, uridylyl-uridine (UpU) and uridylyl-guanosine (UpG), were synthesized on an ABI Model 391 synthesizer on the 0.2 μmol scale. The nucleoside at the 3'-terminus was attached via its 2' (or 3') hydroxyl to a polystyrene solid support with a succinate linker. Wright, et al., *Tetrahedron Lett.*, 34(21):3373–3376 (1993), which is hereby incorporated by reference. The other hydroxyl was protected with an acetyl group. N$^2$ of guanosine was protected with a dimethylformamidine group. The molar excess of phosphoramidite (16), prepared according to Example 9, was 65 to 75 times; tetrazole was used as the activating agent. Coupling times of 5 minutes and 10 minutes were used for UpG synthesis, and 5 minutes for UpU synthesis. In each case, the coupling efficiency based on the DMTr cation assay was greater than 98%. After the synthesis was completed, the resin was treated with 0.5M NaOH for 2 hours at 25° C. After HPLC purification, acid hydrolysis of the intermediate dicarboxylate salt was carried out with dilute HCl (pH 2, 25° C.). Hydrolysis of the 2'-OH protecting group ("HIFA") took place with a half-life of 6 hours. HPLC analysis was on a reverse phase C-18 column using a linear gradient of 0–100% B in 20 minutes at 1.0 ml/min; solvent A=2% acetonitrile in 0.1M TEAA (pH 4.7), solvent B=80% acetonitrile in 0.1M TEAA (pH 4.7). The synthesized UpU and UpG (retention times 6.79 and 6.65 minutes respectively), had the same retention times as authentic samples. The identity of UpG was further confirmed by co-injecting it with an authentic sample. 2'-hydroxyisophthalate formaldehyde acetal (HIFA)-protected UpU and UpG had retention times of 7.33 and 7.23 minutes respectively. The 2'-HIFA protected adenosine monomer was also successfully synthesized. Further, the same synthetic methods can be used to make HIFA-protected C, G and I, either as the methyl or 2-cyanoethyl esters.

Example 11

2'-O-(1-Ethoxyethyl)-3',5'-O-(tetraisopropyldisiloxane-1,3-diyl)uridine (10)

Compound (9), prepared according to Example 1, (500 mg, 1.03 mmol) was dissolved in dry CH$_2$Cl$_2$ (4 ml) and the flask flushed with argon. Ethyl vinyl ether (0.6 ml, 6.3 mmol, 6.1 equiv.) was added followed by a solution of pyridinium p-toluenesulfonate (PPTS)(260 mg, 1.03 mmol) in CH$_2$Cl$_2$ (2 ml). The solution was stirred under argon for 7 hours at room temperature. The crude product was purified by flash chromatography using 1:1 EtOAc:petroleum ether as the eluting solvent. The pure product was obtained as a white foam. The two diastereomers could not be separated on the column and were collected together. NMR of the mixture of the isomers is therefore reported. Yield: 505 mg (88%). $^1$H NMR (CDCl$_3$) δ: 8.45 (br.s, 1 H , NH), 7.96*, 7.92* (d, 1 H, H5 or H6, J$_{5,6}$=8 Hz), 5.78*, 5.69* (s, 1 H, H1'), 5.67 (d, 1 H. H5 or H6, J$_{5,6}$=8 Hz), 5.03 (m, 1 H, CHCH$_3$, 4.30–3.50 (m, 7 H, H2', H3', H4', H5' and OCH$_2$CH3), 1.45*, 1.41* (d, 3 H, CHCH$_3$), 1.24*, 1.20* (q, 3 H, OCH$_2$CH$_3$), 1.2–0.9 (m, 28 H, isopropyls).

* indicates those chemical shifts which are different for the two diastereomers.

Example 12

N$^3$-Benzoyl-2'-O-(1-ethoxyethyl), 3',5'-O-(tetraisopropyldisiloxane-1,3-diyl)uridine Compound (10), prepared according to Example 11, (330 mg, 0.59 mmol) was converted to N$^3$-Benzoyl-2'-O-(1-ethoxyethyl), 3',5'-O-(tetraisopropyldisiloxane-1,3- diyl) uridine by substantially the same method that was used for the synthesis described in Example 3. The crude product was purified by flash chromatography. The column was eluted first with 15:85 EtOAc:petroleum ether and then with 1:3 EtOAc:petroleum ether. The pure product was obtained as a white foam. The two diastereomers were not separated.

Yield: 285 mg (73%) $^1$H NMR (CDCL$_3$) δ:8.08*, 8.04* (d, 1 H, H5 or H6, $J_{5,6}$=8 Hz), 7.98–7.46 (5 H, aryl), 5.80*, 5.70* (s, 1 H, H1'), 5.79 (d, 1 H, H5 or H6, $J_{5,6}$=8 Hz), 4.95 (m, 1 H, CHCH$_3$), 4.35–3.45 (m, 7 H, H2', H3', H4', H5' and OCH$_2$CH$_3$), 1.40 (d, 3 H, CHCH$_3$), 1.2–0.9 (m, 31 H, isopropyls and OCH$_2$CH$_3$)

Example 13

N$^3$-Benzoyl-2'-O-{1-((2-carbomethoxy)phenoxy)ethyl}-3',5'-O-(tetra-isopropyldisiloxane-1,3-diyl) uridine (13)

The compound, prepared according to Example 12, (120 mg, 0.18 mmol) was dissolved in dry CH$_2$Cl$_2$ (1 ml), and the flask was flushed with argon for 10 minutes. Boron trichloride (1M solution in CH$_2$Cl$_2$, 0.11 ml, 0.6 equiv.) was added, and the solution was stirred under argon for 30 minutes at room temperature. The solvent was evaporated, and the crude product was dried in vacuo for 15 minutes. It was stored at −20° C. until further use.

KH (35 wt % oil dispersion, 37 mg, 0.32 mmol, 1.8 equiv.) was suspended in dry toluene (1.5 ml), and the flask was flushed with argon. The suspension was cooled to 0° C., and methyl salicylate (52 mg, 0.34 mmol, 1.9 equiv.) was added. The suspension was stirred for 15 minutes at 0° C. It was then allowed to warm up to room temperature and 18-crown-6 (30 mg, 0.11 mmol, 0.6 equiv) was added. A solution of chloroethyl ether (12), prepared according to Example 12, in dry CH$_2$Cl$_2$ (0.5 ml) was added slowly over a period of 5 minutes. The reaction mixture was stirred under argon for 30 minutes at room temperature. It was then diluted with EtOAc (10 ml) and extracted once with water (10 ml). The aqueous layer was back extracted with EtOAc (2×10 ml). Organic extracts were pooled, washed once with brine (5 ml), and dried over anhydrous MgSO$_4$. The crude product was purified by flash chromatography. The column was eluted first with 85:15 petroleum ether: EtOAc (75 ml) and then with 2:1 petroleum ether:EtOAc. Yield: 35 mg (25%). $^1$H NMR (CDCl$_3$) δ: 7.98–6.97 (10 H, aryl and H5 or H6), 5.79*, 5.72* (s, 1 H, H1'), 5.77*, 5.75* (d, 1 H, H5 or H6), 5.67 (q, 1 H, CHCH$_3$), 4.45–3.90 (m, 5 H H2' H3', H4' and H5'), 3.81 (s, 3 H, CO$_2$CH$_3$), 1.61*, 1.49* (d, 3 H, CHCH$_3$, 1.2–0.9 (m, 28 H, isopropyls).

Example 14

N$^3$-Benzoyl-2'-O-{1-((2-carbomethoxy)phenoxy) ethyl}uridine (14)

Compound (13), prepared according to Example 13, (65 mg, 0.09 mmol) was converted to N$^3$-Benzoyl-2'-O-{1-((2-carbomethoxy)phenoxy)ethyl}uridine (14) by substantially the same method that was used for the synthesis in Example 7. The crude product was purified by flash chromatography. The column was eluted first with 85:15 EtOAc:petroleum ether (50 ml) and then with 4% methanol in EtOAc.

Yield: 40 mg (89%). 1H NMR (CDCl$_3$) δ: 7.94–6.88 (10 H, aryl and H5 or H6), 5.87–5.71 (m, 3 H, H1' H5 or H6 and CHCH$_3$), 4.83 (t, 1 H, H2' or 3'), 4.35–4.10 (m, 2 H, H2' or H3, and H4), 3.88 (s, 3 H, CO$_2$CH$_3$), 3.80 (q, 2 H, H5'), 1.57*, 1.53* (d, 3 H, CHCH$_3$)

Example 15

The rate of acetal hydrolysis of compound (14), both as the bis ester, and the bis acid was studied. At each pH value, four or five readings were taken of the percentage of acetal remaining vs. time, and each set of points was fitted to an integrated first-order rate equation by an unweighted least squares method. The results are shown below in Table 1. The half-life for hydrolysis of the bis ester acetal (14) in dilute HCl (pH 1, 25° C.) was 86 hours. The methyl esters and the N$^3$-benzoyl group of (14) were hydrolyzed with 0.2N NaOH, and the resulting dicarboxylate salt was purified by HPLC and subjected to the acid hydrolysis. In tests with methyl esters, aqueous sodium hydroxide was used to hydrolyze the esters, as concentrated ammonia gave more amide (60%) than carboxylic acid (40%). However, ammonia-ethanol (3:2 v/v) can be used with 2-cyanoethyl esters, as β-elimination gives the carboxylic acid directly. Rastogi, Ph.D. Thesis, Cornell University, Ithaca, N.Y. (1995), which is hereby incorporated by reference. Conversion of the bis ester to the bis carboxylic acid increased the rate of acid-catalyzed hydrolysis of the acetal by 42-fold at pH 1; by extrapolation (Dunn, et al. *J. Am. Chem. Soc.*, 92(8): 2410–2416 (1970) ("Dunn"), which is hereby incorporated by reference), the corresponding rate increase at pH 3 would be 1,320. For the bis acid, the rate drops by a factor of only 3.1 on going from pH 1 to pH 3.

A comparison of hydroxyisophthalic acid formaldehyde acetal ("HIFA") with some other acetal-based protecting groups is also presented below in Table 1. All these studies were conducted on uridine having free 31 and 5' hydroxyls.

At a pH of 1, the bis-ester form of HIFA is much more stable than either 1-(2-fluorophenyl)-4-methoxypiperidin-4-yl ("Fpmp"), 1-(2-chloro-4-methlyphenyl)-4-methoxypiperidin-4-yl ("Ctmp"), or 4-methoxytetrahydropyran-4-yl ("Mthp"). This is significant, because strongly acidic conditions are repeatedly employed for removing the dimethoxytrityl groups during oligomer synthesis, and yet the 2'-protecting group must stay in place. Indeed, Rozners et al., *Nucleic Acids Res.*, 22(1): 94–99 (1994), which is hereby incorporated by reference, claim that Fpmp and Ctmp are insufficiently stable when used for oligomer synthesis using the H-phosphonate method. The bis ester form of HIFA is 112 times more stable than Fpmp at a pH of 1, and, if the rate of hydrolysis of the bis ester is first order in H+ in this pH region (Dunn), then HIFA would be 3,100 times more stable than Fpmp at pH 3. After base-catalyzed hydrolysis of the bis ester to the bis acid, the HIFA acetal becomes much more labile and is within a factor of 2.35 of the rate of hydrolysis of Fpmp at pH 3.

With other acetal protecting groups, the ratio of rates of hydrolysis at pH 1 and pH 3 is significant;

this ratio should be as low as possible. Ctmp (ratio=2.25) and Fpmp (ratio=3.6) are clearly better than Mthp (ratio=140). However, HIFA (ratio=0.076) is better still, for this ratio is calculated from the rate for the bis-ester at a pH of 1 and the bis acid at a pH of 3. The "ratio of ratios" for Fpmp and HIFA (3.6/0.076) shows that HIFA has the better figure by a factor of 47.

TABLE 1

Comparison of hydroxyisophthalic acid formaldehyde acetal (HIFA) with other acetal-based protecting groups

| 2'-OH protecting group on uridine | $t_{1/2}$ at 25° C. | | |
|---|---|---|---|
| | pH 1 | pH 2 | pH 3 |
| HIFA (bis ester) | 86 h | — | — |
| HIFA (bis acid) | 124 min | 201 min | 390 min |
| Mthp | 0.9 min | 20.5 min | 126 min |
| Ctmp | 35.5 min | 40 min | 80 min |
| Fpmp | ~ 46 min | ~ 52 min | 166 min |

The data for Mthp and Ctmp were taken from Reese et al., Tetrahedron Lett., 27(20):2291–2294 (1986), which is hereby incorporated by reference. The data for Fpmp were taken from Rao, et al, J. Chem. Soc., Perkin Trans. 1:43–55 (1993), which is hereby incorporated by reference.

Although the invention has been described in detail for the purpose of illustration, it is understood that such detail is solely for that purpose and variations can be made therein by those skilled in the art without departing from the spirit and the scope of the invention which is defined by the following claims.

What is claimed:

1. A nucleoside having the formula:

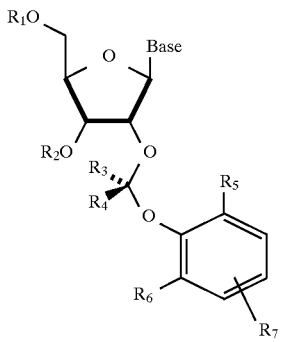

where

R$_1$ is a hydrogen or a protecting group;

R$_2$ is a hydrogen or a phosphoramidite coupling group;

R$_3$ and R$_4$ are each either a hydrogen or an alkyl group, where R$_3$ and R$_4$ can be connected in a ring;

R$_5$ is a hydrogen, an alkyl group, or a carboxylic ester group;

R$_6$ is a hydrogen, an alkyl group, or a carboxylic ester group;

R$_7$ is a hydrogen, a nitro group, a halogen, a cyano group, or an alkyl group, where R$_7$ is attached at either position 4, 5, or 6; and Base is a protected or unprotected heterocyclic base.

2. The nucleoside according to claim 1, wherein R$_1$, R$_2$, R$_3$, R$_4$, R$_7$ are hydrogen, and R$_5$ and R$_6$ are a carboxylic ester group.

3. The nucleoside according to claim 2, wherein R$_5$ and R$_6$ are CO$_2$CH$_3$.

4. The nucleoside according to claim 1, wherein R$_1$, R$_2$, R$_3$, R$_4$, R$_5$ and R$_7$ are hydrogen and R$_6$ is CO$_2$CH$_2$CH$_2$CN.

5. The nucleoside according to claim 1, wherein R$_1$ and R$_2$ are hydrogen, one of either R$_3$ or R$_4$ is an alkyl group and the other is hydrogen, R$_5$ is CO$_2$CH$_3$, and R$_6$ and R$_7$ are hydrogen.

6. The nucleoside according to claim 1, wherein R$_1$ is dimethoxytrityl, R$_2$ is 2-cyanoethyl N,N-diisopropylphosphoramidite, R$_3$, R$_4$, and R$_7$ are hydrogen, and R$_5$ and R$_6$ are CO$_2$CH$_3$.

7. The nucleoside according to claim 1, wherein Base is thymin-1-yl.

8. The nucleoside according to claim 1, wherein Base is adenin-9-yl.

9. The nucleoside according to claim 1, wherein Base is guanin-9-yl.

10. The nucleoside according to claim 1, wherein Base is cytosin-1-yl.

11. The nucleoside according to claim 1, wherein Base is uracil-1-yl.

12. The nucleoside according to claim 1, wherein Base is hypoxanthin-9-yl.

13. A nucleoside having the formula:

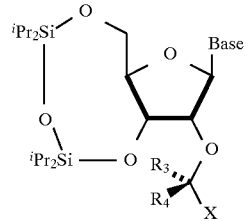

where R$_3$ and R$_4$ are each either a hydrogen or an alkyl group, where R$_3$ and R$_4$ can be connected in a ring;

X is a methylthio group; and

Base is a protected or unprotected heterocyclic base.

14. A nucleoside having the formula:

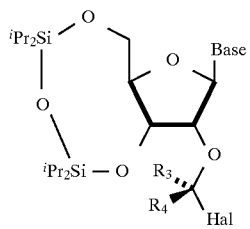

where R$_3$ and R$_4$ are each either a hydrogen or an alkyl group, where R$_3$ and R$_4$ can be connected in a ring;

Hal is any halogen; and

Base is a protected or unprotected heterocyclic base.

15. A method of producing a fully protected nucleoside comprising:

providing a 5'-OH protected nucleoside having the formula:

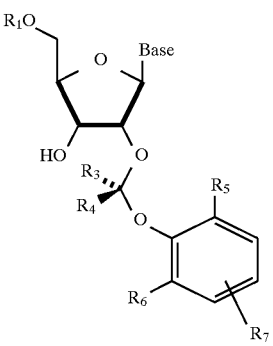

where $R_1$ is a hydrogen or a protecting group;
$R_3$ and $R_4$ are each either a hydrogen or an alkyl group, where $R_3$ and $R_4$ can be connected in a ring;
$R_5$ is a hydrogen, an alkyl group, or a carboxylic ester group;
$R_6$ is a hydrogen, an alkyl group, or a carboxylic ester group;
$R_7$ is a hydrogen, a nitro group, a halogen, a cyano group, or an alkyl group, where $R_7$ is attached at either position 4, 5 or 6; and
Base is a protected heterocyclic base;
providing a phosphoramidite coupling group; and
reacting the 5'-OH protected nucleoside and the phosphoramidite coupling group under conditions effective to produce the fully protected nucleoside having the formula:

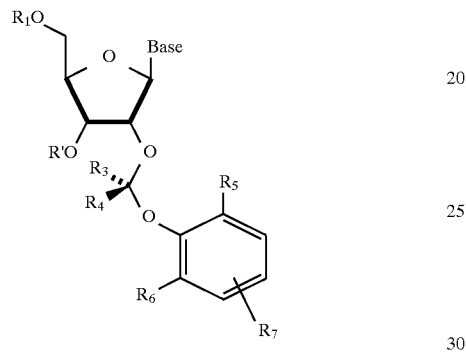

where
$R_1$ is a hydrogen or a protecting group;
R' is a phosphoramidite coupling group;
$R_3$ and $R_4$ are each either a hydrogen or an alkyl group, where $R_3$ and $R_4$ can be connected in a ring;
$R_5$ is a hydrogen, an alkyl group, or a carboxylic ester group;
$R_6$ is a hydrogen, an alkyl group, or a carboxylic ester group;
$R_7$ is a hydrogen, a nitro group, a halogen, a cyano group, or an alkyl group, where $R_7$ is attached at either position 4, 5 or 6; and
Base is a protected heterocyclic base.

16. The method according to claim 15, wherein said providing the 5'-OH protected nucleoside which further comprises:
providing a 2'-OH protected nucleoside having the formula:

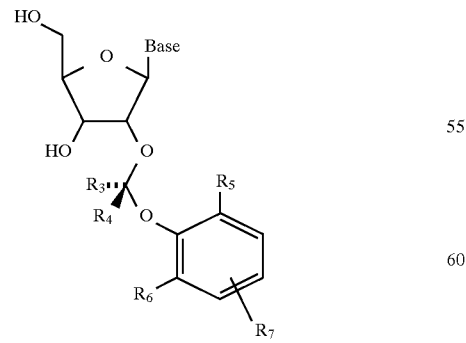

where
$R_3$ and $R_4$ are each either a hydrogen or an alkyl group, where $R_3$ and $R_4$ can be connected in a ring;
$R_5$ is a hydrogen, an alkyl group, or a carboxylic ester group;
$R_6$ is a hydrogen, an alkyl group, or a carboxylic ester group;
$R_7$ is a hydrogen, a nitro group, a halogen, a cyano group, or an alkyl group, where $R_7$ is attached at either position 4, 5 or 6; and
Base is a protected heterocyclic base;
providing a protecting group; and
reacting the 2'-OH nucleoside and the protecting group under conditions effective to produce the 5'-OH protected nucleoside;

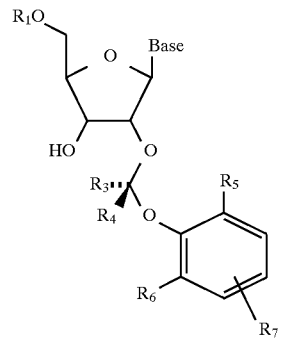

where
$R_1$ is a hydrogen or a protecting group;
$R_3$ and $R_4$ are each either a hydrogen or an alkyl group, where $R_3$ and $R_4$ can be connected in a ring;
$R_5$ is a hydrogen, an alkyl group, or a carbolic ester group:
$R_6$ is a hydrogen, an alkyl group, or a carboxylic ester group;
$R_7$ is a hydrogen, a nitro group, a halogen, a cyano group, or an alkyl group, where $R_7$ is attached at either position 4, 5 or 6; and
Base is a protected heterocyclic base.

17. The method according to claim 16, wherein said providing the 2'-OH protected nucleoside which further comprises:
providing a nucleoside having the formula:

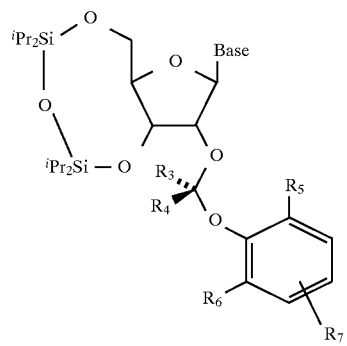

where
$R_3$ and $R_4$ are each either a hydrogen or an alkyl group, where $R_3$ and $R_4$ can be connected in a ring;
$R_5$ is a hydrogen, an alkyl group, or a carboxylic ester group;
$R_6$ is a hydrogen, an alkyl group, or a carboxylic ester group;
$R_7$ is a hydrogen, a nitro group, a halogen, a cyano group, or an alkyl group where $R_7$ is attached at either position 4, 5 or 6; and Base is a protected heterocyclic base;

providing tetrabutyl ammonium fluoride; and reacting the nucleoside and tetrabutyl ammonium fluoride under conditions effective to produce the 2'-OH protected nucleoside:

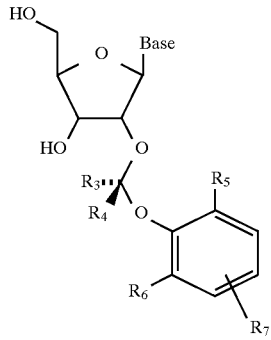

where $R_3$ and $R_4$ are each either a hydrogen or an alkyl group, where $R_3$ and $R_4$ can be connected in a ring;

$R_5$ is a hydrogen, an alkyl group, or a carboxylic ester group;

$R_6$ is a hydrogen, an alkyl group, or a carboxylic ester group;

$R_7$ is a hydrogen, a nitro group, a halogen, a cyano group, or an alkyl group, where $R_7$ is attached at either position 4, 5 or 6; and Base is a protected heterocyclic base.

18. The method according to claim 15, wherein $R_3$, $R_4$, and $R_7$ are hydrogen, and $R_5$ and $R_6$ are each a carboxylic ester group.

19. The method according to claim 18, wherein $R_3$, $R_4$, and $R_7$ are hydrogen and $R_5$ and $R_6$ are $CO_2CH_3$.

20. The method according to claim 15, wherein $R_3$, $R_4$, $R_5$, and $R_7$ are hydrogen and $R_6$ is $CO_2CH_2CH_2CN$.

21. The method according to claim 15, wherein one of either one either $R_3$ or $R_4$ is an alkyl group and the other is hydrogen, $R_5$ is $CO_2CH_3$, $R_6$ and $R_7$ are hydrogen.

22. The method according to claim 15, wherein $R_1$ is dimethoxytrityl, $R_2$ is 2-cyanoethyl N,N-diisopropylphosphoramidite, $R_3$, $R_4$, and $R_7$ are hydrogen, and $R_5$ and $R_6$ are $CO_2CH_3$.

23. The method according to claim 15, wherein Base is thymin-1-yl.

24. The method according to claim 15, wherein Base is adenin-9-yl.

25. The method according to claim 15, wherein Base is guanin-9-yl.

26. The method according to claim 15, wherein Base is cytosin-1-yl.

27. The method according to claim 15, wherein Base is uracil-1-yl.

28. The method according to claim 15, wherein Base is hypoxanthin-9-yl.

29. The method of claim 17, wherein providing the nucleoside further comprises:

providing a haloalkyl ether having the formula:

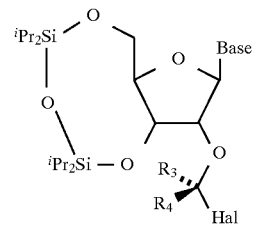

where $R_3$ and $R_4$ are each either a hydrogen or an alkyl group, where $R_3$ and $R_4$ can be connected in a ring;

Hal is any halogen; and

Base is a protected heterocyclic base;

providing a salt of a phenol; and reacting the haloalkyl ether and the salt of a phenol under conditions effective to produce the nucleoside;

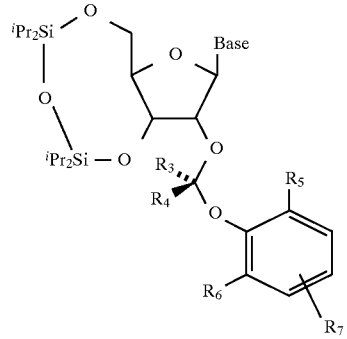

where $R_3$ and $R_4$ are each either a hydrogen or an alkyl group, where $R_3$ and $R_4$ can be connected in a ring;

$R_5$ is a hydrogen, an alkyl group, or a carboxylic ester group;

$R_6$ is a hydrogen, an alkyl group, or a carboxylic ester group;

$R_7$ is a hydrogen, a nitro group, a halogen, a cyano group, or an alkyl group where $R_7$ is attached at either position 4, 5 or 6; and Base is a protected heterocyclic base.

30. The method of claim 29, wherein said providing the haloalkyl ether which further comprises:

providing an ether having the formula:

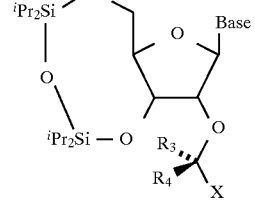

where $R_3$ and $R_4$ are each either a hydrogen or an alkyl group, where $R_3$ and $R_4$ can be connected in a ring;

Base is a protected heterocyclic base; and

X is either ethoxy or methylthio;

providing a halogenating reagent (e.g. boron trichloride when X is ethoxy or sulfuryl chloride when X is methylthio); and reacting the ether and the halogenating reagent under conditions effective to produce the haloalkyl ether;

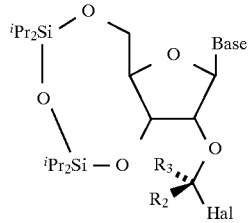

where
R₃ and R₄ are each either a hydrogen or an alkyl group, where R₃ and R₄ can be connected in a ring;
Hal is any halogen; and
Base is a protected heterocyclic base.

31. The method of claim 30, wherein said providing the ether further comprises:
providing an ether having the formula:

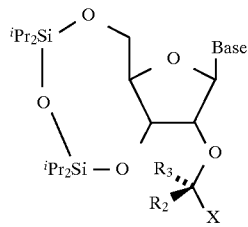

where
R₃ and R₄ a each either a hydrogen or an alkyl group, where R₃ and R₄ can be connected in a ring;
Base is a heterocyclic base, and
X is either ethoxy or methylthio;
providing a base protecting group and
reacting the ether with the base protecting group under conditions effective to produce the ether:

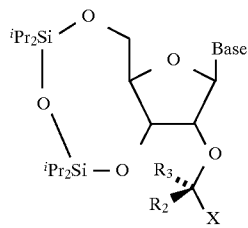

where
R₃ and R₄ each either a hydrogen or an alkyl group, where R₃ and R₄ can be connected in a ring;
Base is a protected heterocyclic base, and
X is either ethoxy or methylthio.

32. The method of claim 31, wherein said providing the ether further comprises:

providing a monomer having the formula:

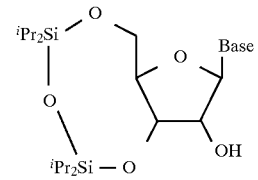

where
Base is a heterocyclic base;
providing either ethyl vinyl ether or DMSO with acetic anhydride and acetic acid; and
reacting the monomer and either the ethyl vinyl ether, or the DMSO with acetic anhydride and acetic acid, under conditions effective to produce the ether;

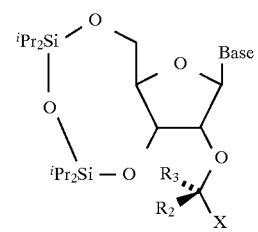

where
R₃ and R₄ are each either a hydrogen or an alkyl group, where R₃ and R₄ can be connected in a ring;
Base is a heterocyclic base; and
X is either ethoxy or methylthio.

33. The method of claim 32, wherein said providing a monomer further comprises:
providing a compound having the formula:

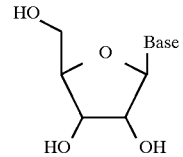

where
Base is a heterocyclic base;
providing 1,3-dichloro-1,1,3,3, tetraisopropyldisiloxane; and
reacting the compound and the 1,3-dichloro-1,1,3,3, tetraisopropyldisiloxane under conditions effective to produce the monomer:

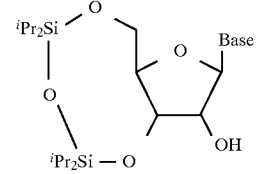

where
Base is a heterocyclic base.

34. A method of oligomer synthesis comprising:
providing a nucleoside covalently attached to a solid support and repeatedly reacting the nucleoside with said nucleoside of claim 1 under conditions effective to produce the oligomer of the following formula:

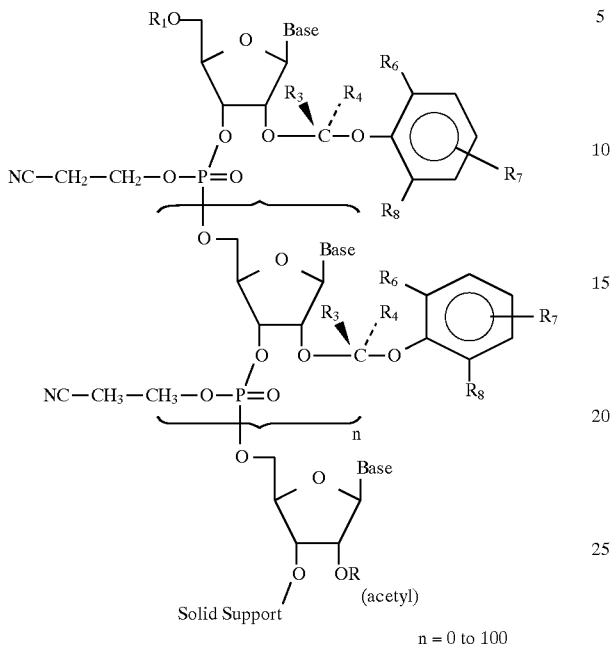

Solid Support n = 0 to 100 where
- $R_1$ a hydrogen or a protecting group;
- $R_3$ and $R_4$ are each either a hydrogen or an alkyl group, where $R_3$ and $R_4$ can be connected in a ring;
- $R_5$ is a hydrogen, an alkyl group, or a carboxylic ester group;
- $R_6$ is a hydrogen, an alkyl group, or a carboxylic ester group;
- $R_7$ is a hydrogen, a nitro group, a halogen, a cyano group, or an alkyl group, where $R_7$ is attached at either position 4, 5, or 6; and
- Base is a protected or heterocyclic base.

35. A nucleoside having the formula:

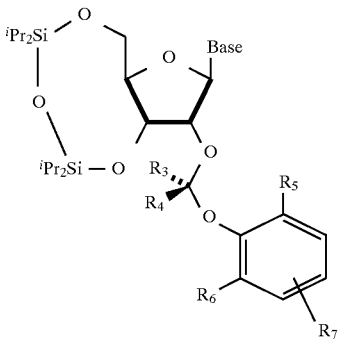

where
- $R_3$ and $R_4$ are each either a hydrogen or an alkyl group, where $R_3$ and $R_4$ can be connected in a ring;
- $R_5$ is a hydrogen, an alkyl group, or a carboxylic ester group;
- $R_6$ is a hydrogen, an alkyl group, or a carboxylic ester group;
- $R_7$ is a hydrogen, a nitro group, a halogen, a cyano group, or alkyl group where $R_7$ is attached at either position 4, 5 or 6; and
- Base is a protected heterocyclic base.

* * * * *